United States Patent [19]

Christopher

[11] Patent Number: 4,869,597
[45] Date of Patent: Sep. 26, 1989

[54] CALORIMETER

[76] Inventor: Daniel E. Christopher, 4584 Power Blvd., Decatur, Ill. 62521

[21] Appl. No.: 206,439

[22] Filed: Jun. 13, 1988

[51] Int. Cl.[4] .......................................... G01N 25/40
[52] U.S. Cl. ......................................... 374/37; 374/36
[58] Field of Search ............................... 374/31, 36–42

[56] References Cited

U.S. PATENT DOCUMENTS

| | | | |
|---|---|---|---|
| 494,057 | 3/1893 | Carpenter | 374/42 |
| 987,537 | 3/1911 | Beasley et al. | 374/36 |
| 1,150,836 | 8/1915 | Doherty | 374/36 |
| 1,189,300 | 7/1916 | Smith | 374/36 |
| 1,607,684 | 11/1926 | Morehead | 374/36 |
| 1,678,918 | 7/1928 | Schmidt | 374/36 |
| 1,778,958 | 10/1930 | Parr | 374/36 |
| 1,997,383 | 4/1935 | Junkers | 374/36 |
| 2,141,453 | 12/1938 | Schmidt | 374/36 |
| 2,177,267 | 10/1939 | Stewart | 222/4 |
| 2,238,606 | 4/1941 | Schmidt | 374/36 |
| 2,349,517 | 5/1944 | Pinkerton | 374/36 |
| 2,743,609 | 5/1956 | Schuller | 374/36 |
| 4,329,874 | 5/1982 | Maeda | 374/36 |
| 4,384,792 | 5/1983 | Sommers et al. | 374/36 |
| 4,433,922 | 2/1984 | Bohl et al. | 374/36 |
| 4,500,214 | 2/1985 | Calvet et al. | 374/36 |
| 4,531,843 | 6/1985 | Kuhnlein et al. | 374/40 |
| 4,720,196 | 1/1988 | Mondeil et al. | 374/37 |

FOREIGN PATENT DOCUMENTS 12615 of 1907 United Kingdom ................. 374/42

Primary Examiner—William A. Cuchlinski, Jr.
Assistant Examiner—W. Morris Worth
Attorney, Agent, or Firm—Wood, Dalton, Phillips Mason & Rowe

[57] ABSTRACT

A calorimeter of the liquid flow type. The calorimeter includes a chamber in communication with a medium to be delivered to the chamber at a steady rate of flow. It also includes a heat exchanger having a liquid flowing therethrough at a steady rate of flow in a non-recirculating manner. The chamber is submerged within the heat exchanger and formed so as to release the heating medium from the chamber into the liquid as the liquid is flowing through the heat exchanger. The calorimeter also is capable of measuring an increase in temperature from a first point to a second point as the liquid is flowing at a steady rate through the heat exchanger. As a result, the calorimeter can measure the heating value of a heating medium at preselected intervals or continuously.

21 Claims, 2 Drawing Sheets

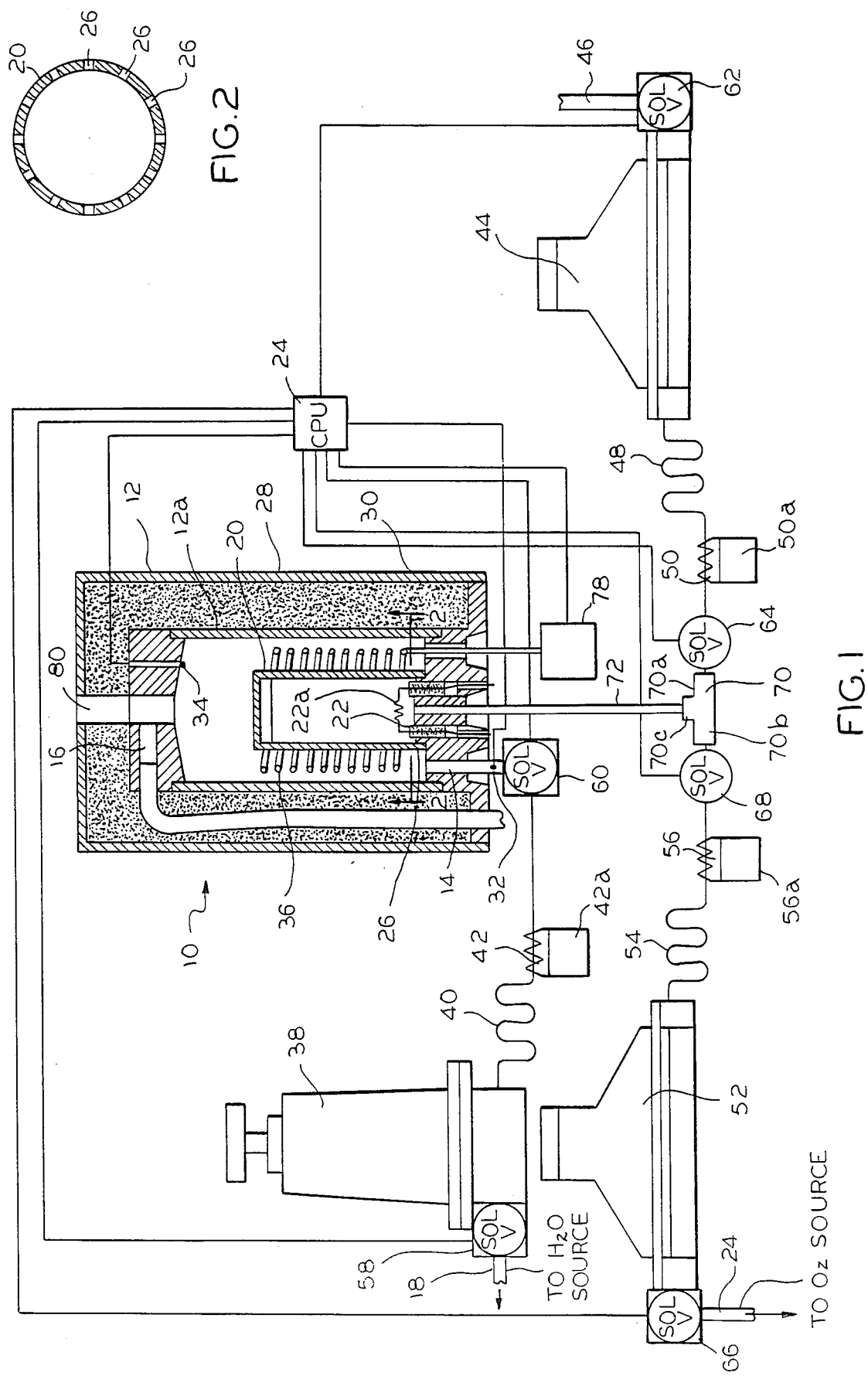

CALORIMETER

FIELD OF THE INVENTION

The present invention relates to heat measuring devices and, more particularly, a calorimeter of the liquid-flow type.

BACKGROUND OF THE INVENTION

In earlier years, natural gas was often a nuisance to producers and was burned as a convenient method of disposal. At that time, it was valued at a manufacturing cost of only a few cents per thousand cubic feet. As prices rose, the accuracy of measurement became more important and represented a potentially significant economic loss at every custody transfer point.

Initially, there were few measurement systems although orifice measurement was adopted by the American Gas Association. Venturi nozzles provided good results but were too expensive and needed calibration which was not available in larger sizes. Turbine meters were also available but it was generally accepted that they lacked the necessary degree of accuracy that would permit them to be trusted. As time passed, still other types of meters were introduced and manufacturers were attempting to establish their claims of accuracy.

During these years, those who were buying and selling natural gas have relied on various types of measuring devices. Calibrated liquid filled thermometers have given way to thermocouples and RTD's, pressure gauges have been replaced by pressure transducers and in addition a multitude of special devices have been utilized including gravitometers, densitometers, moisture analyzers and viscosimiters. During this time, the heating value of natural gas was considered, but the difficulty of measurement precluded its widespread use.

Principally, batch calorimeters were known to be available but continuous measurement was at this time first being proposed by Cutler-Hammer. For instance, continuous measurement is contemplated by Cutler-Hammer U.S. Pat. No. 2,238,606 but, while capable of continuous measurement, this device was never in great demand due primarily to its high cost and, in addition, because it required an air conditioned environment for successful operation. Moreover, the Cutler-Hammer device was a large and complicated machine requiring technically qualified operators, high maintenance costs, and a reference gas for calibration.

Nevertheless, the Cutler-Hammer device was considered a standard in the industry until the development of the gas chromatograph. This device does not measure heating value but, rather, does a quantitative chemical analysis. In this manner, the theoretical heating value can be obtained by taking the sum of the values of the different components of the gas.

Among the advantages of the gas chromatograph is its small size and the fact that it does not require an air conditioned environment. It does, however, require a technically trained operator, a certified reference gas and a carrier gas. While its value is recognized by those in the field, the gas chromatograph is limited in usage by a number of considerations, including cost.

In addition to measuring the heating value of a gas, it would also be desirable to measure the heating value of other heating media. This is true in particular of steam since there are many applications in which steam is used for processing and/or heating. However, there has been no truly accurate and effective way of accomplishing this objective.

In view of the foregoing, it has remained to provide a simple, inexpensive calorimeter for measuring the heating value of a heating medium such as gas or steam. In addition, there has been no such calorimeter that can be operated as a stand-alone device with automatic calibration and data transmission to a central processor which can be used particularly effectively at all points in the chain of custody transfer of natural gas from the gas well to the ultimate user. As a result, these are among the principal objects of the present invention as will be apparent from a consideration of the unique features as described hereinafter.

Moreover, since over 95% of all natural gas is used for heating, it follows that gas composition is of little importance in most instances. Thus, it is desirable to avoid the high cost of the gas chromatograph so long as the heating value of gas can be determined at the same or comparable levels of accuracy. Still further, in contrast to the gas chromatograph, it would be desirable to eliminate the need for instruments such as gravitometers, densitometers, moisture analyzers and viscosimiters.

Still further objects of the present invention are automatic calibration and the ability to measure the heating value of a gas at preselected intervals or continuously.

SUMMARY OF THE INVENTION

Accordingly, the present invention is directed to a calorimeter of the liquid-flow type for measuring the heating value of a heating medium such as gas or steam at preselected intervals or continuously. The calorimeter includes a steam chamber or, in the case of gas, a combustion chamber having a burner in communication with the gas and with oxygen to be delivered to the burner at a steady rate of flow. It also includes in both cases a heat exchanger having a liquid flowing therethrough at a steady rate of flow in a non-recirculating manner. The calorimeter is designed such that the steam or combustion chamber is submerged within the heat exchanger and such that the steam or combustion chamber includes means for releasing the steam or the products of combustion from burning the gas and oxygen. It also includes in both cases means for measuring an increase in temperature from a first point to a second point as the liquid is flowing at a steady rate through the heat exchanger. Since the releasing means causes the steam or products of combustion to pass from the steam chamber or combustion chamber into the liquid, all heat from the heating medium is transferred to the liquid and the heating value of the heating medium can be determined with the calorimeter.

In the preferred embodiment, the heat exchanger includes a liquid inlet at one end thereof and a liquid outlet at the other end thereof, and the combustion chamber is mounted adjacent the liquid inlet so as to be entirely disposed below the liquid outlet. The heat exchanger and combustion chamber are both preferably defined by generally cylindrical shells and the heat exchanger is advantageously disposed within a generally cylindrical reactor shell spaced from the heat exchanger to define a thermal barrier filled with thermal insulation therebetween. With this arrangement, the releasing means preferably includes a plurality of chamber outlets disposed about the generally cylindrical shell which defines the combustion chamber preferably at a point adjacent the liquid inlet for release of the products of combustion into the liquid well before the liquid reaches the liquid outlet.

Still further, the temperature measuring means is preferably integrally associated with a central processing unit which is responsive to operation of calibration means to relate temperature difference to heating value. The central processing unit is then advantageously later responsive to burning of the gas and oxygen to convert temperature difference to the heating value of the gas. Additionally, the central processing unit is programmable to use the calibration means to calibrate the calorimeter and/or to measure the heating value of the gas at preselected intervals or continuously.

Still other objects, advantages and features of the present invention will become apparent from a consideration of the following specification taken in conjunction with the accompanying drawings.

BRIEF DESCRIPTION OF THE DRAWINGS

FIG. 1 is a cross-sectional view, partially schematic, illustrating a calorimeter in accordance with the present invention;

FIG. 2 is a cross-sectional view taken on the line 2—2 of FIG. 1 illustrating a feature of the calorimeter combustion chamber;

DETAILED DESCRIPTION OF THE PREFERRED EMBODIMENT

Figure 4:
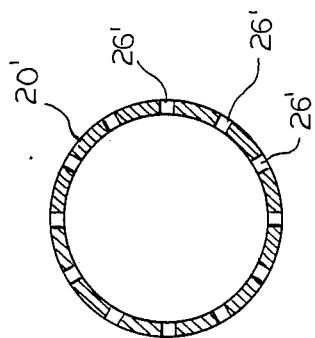
FIG. 4 is a cross-sectional view taken on the line 4—4 of FIG. 3 illustrating a feature of the calorimeter steam chamber.

In the drawings, and with reference first to FIG. 1, the reference numeral 10 designates generally a calorimeter of the liquid flow type in accordance with the present invention. The calorimeter 10 includes a heat exchanger 12 having a liquid inlet 14 and a liquid outlet 16 in spaced apart relation. As shown, the heat exchanger 12 is in communication with a source of liquid under pressure as at 18 at the liquid inlet 14 and the liquid outlet 16 is adapted to carry the liquid away from the heat exchanger 12.

Still referring to FIG. 1, the calorimeter 10 includes means provided for ensuring a steady rate of flow of the liquid from the liquid inlet 14, through the heat exchanger 12, and out the liquid outlet 16 as will be described in greater detail hereinafter. The calorimeter 10 also includes a combustion chamber 20 having a burner 22 within the heat exchanger 12. The combustion chamber 20 is entirely disposed below the liquid outlet 16 so as to be submerged in the liquid when the liquid is flowing through the heat exchanger 12 at a steady rate of flow. Means are also provided for ensuring a steady rate of flow of gas to the burner 22 as will be described hereinafter. The calorimeter 10 further includes a source of oxygen 24 under pressure for mixture with the gas. The oxygen and gas are adapted to be burned at the burner 22 in the combustion chamber 20 to heat the liquid from a first temperature at the liquid inlet 14 to a second, higher temperature at the liquid outlet 16 as the liquid is flowing through the heat exchanger 12 at a steady rate of flow. Means are further provided for ensuring a steady rate of flow of the oxygen to the burner 22 as will be described in greater detail hereinafter. In addition, the calorimeter is preferably formed such that the combustion chamber 20 includes means such as the chamber outlets 26 for releasing the products of combustion for burning the oxygen and gas at the burner 22 (see, also, FIG. 2).

As will be appreciated, the chamber outlets 26 cause the products of combustion to pass from the combustion chamber 20 into the liquid as the liquid is flowing through the heat exchanger 12 at a steady rate of flow. The chamber outlets 26 ensure that all heat from the oxygen and gas, including that produced from burning the oxygen and gas as well as the products of combustion and that absorbed in any excess oxygen, is transferred directly to the liquid. As a result, the calorimeter 10 can utilize means for measuring the difference between the first and second temperatures to accurately determine the heating value of the gas at preselected intervals or continuously.

As shown, the liquid inlet 14 is disposed at one end of the heat exchanger 12 and the liquid outlet 16 is disposed at the other end thereof with the combustion chamber 20 being mounted adjacent the liquid inlet end 14. By reason of the relative size of the combustion chamber 20 and the heat exchanger 12, the combustion chamber 20 will be entirely disposed below the liquid outlet 16 whereby the entire combustion chamber is submerged during operation of the calorimeter 10. In other words, the combustion chamber 20 is in spaced relation to the liquid outlet end of the heat exchanger 12 which causes it to be submerged since the heat exchanger 12 is entirely filled with liquid at all times during operation.

As will be appreciated, the combustion chamber 20 and the heat exchanger 12 are defined by generally cylindrical inner and outer shells preferably disposed so as to be in coaxial relation as shown in FIG. 1. The chamber outlets 26 are provided substantially entirely about the generally cylindrical shell defining the combustion chamber 20 and preferably in a ring at or near the level of the liquid inlet 14 and the burner 22. Furthermore, the heat exchanger 12 preferably includes a water jacket 12a disposed within a generally cylindrical reactor shell 28 which is spaced from the heat exchanger 12 to define a thermal barrier that is filled with insulation 30.

Referring specifically to FIG. 1, the temperature measuring means includes a first liquid temperature detecting thermistor 32 disposed at a first point in the heat exchanger 12 and a second liquid temperature detecting thermistor 34 disposed at a second point in the heat exchanger 12. It will also be seen that means for calibrating the calorimeter 10 including a calibration heater 36 is provided for correlating known energy inputs of the heater 36 to measured temperature increases between the first point in the heat exchanger 12 and the second point in the heat exchanger 12 whereby the calibration is then used to accurately determine the heating value of the gas. In other words, the calibration heater 36 makes it possible to calibrate the calorimeter 10 for converting a measured temperature difference between the first end or liquid inlet end 14 and the second end or liquid outlet end 16 of the heat exchanger 12 into the heating value of gas burned at the burner 22.

As will be appreciated, the steady liquid flow means includes a liquid pressure regulator 38 disposed between the source of liquid as at 18 and the liquid inlet 14 as well as a liqid capillary flow tube 40 and a liquid heater 42 intermediate the liquid pressure regulator 38 and the liquid inlet 14. It will also be seen that the steady gas flow means includes a gas pressure regulator 44 disposed between the gas as at 46 and the burner 22 and further includes a gas capillary flow tube 48 and a gas heater 50 intermediate the gas pressure regulator 44 and the burner 22. Additionally, the steady oxygen flow means includes an oxygen pressure regulator 52 disposed between the source of oxygen as at 24 and the burner 22 as well as an oxygen capillary flow tube 54 and an oxygen heater 56 intermediate the oxygen pressure regulator 52 and the burner 22.

With these features, there is also preferably provided first and second liquid solenoid valves 58 and 60 arranged as illustrated. It will also be seen in FIG. 1 that gas solenoid valves 62 and 64 are provided on either side of the steady gas flow means, i.e., the gas pressure regulator 44, gas capillary flow tube 48, and gas heater 50. Still further, there is also preferably provided oxygen solenoid valves 66 and 68 arranged as illustrated.

With the arrangement of components as shown, oxygen and gas are preferably mixed at a T-fitting 70 from which the mixture is delivered to the burner 22. This T-fitting 70 has a first portion 70a in communication with the gas as at 46 through solenoid valve 62, gas pressure regulator valve 44, gas capillary flow tube 48, gas heater 50 and gas solenoid valve 64, and it also has a second portion 70b in communication with the source of oxygen as at 24 through the oxygen solenoid valve 66, oxygen pressure regulator 52, oxygen capillary flow tube 54, oxygen heater 56, and oxygen solenoid valve 68. With this arrangement, the T-fitting 70 communicates with the burner 22 through a third portion 70c and a mixed gas flow tube 72 extending therebetween.

While the calorimeter 10 can be operated by manual control of the valves to measure the gas heating value, a central processing unit 74 can advantageously achieve this objective automatically to great advantage either on demand, at selected intervals or continuously. Thus, the thermistors 32 and 34 are preferably operatively associated with the central processing unit 74, as shown, and the central processing unit 74 is preferably responsive to operation of the calibration heater 36 which is disposed about the combustion chamber 20. Specifically, the calibration heater 36 is linked to a control unit 78 which is located externally of the heat exchanger 12, and the central processing unit 74 can thus be calibrated by measuring the temperature difference of a known energy input to later convert a measured temperature difference directly to the heating value of a gas burned with oxygen at the burner 22.

Moreover, as shown, the central processing unit 74 is preferably operably associated with the valves 58, 62 and 66 as well as the valves 60, 64 and 68 to control delivery of the liquid to the heat exchanger 12 and delivery of the gas and oxygen to the combustion chamber 20 during operation of the calorimeter 10. For this purpose, the central processing unit 74 is preferably of a conventional type which is programmable to calibrate the calorimeter 10 by setting the control unit 78 to operate the calibration heater 36 as liquid flows through the heat exchanger 12 and/or to measure the heating value of the gas as the liquid flows through the heat exchanger 12 and the gas and oxygen are burned in the combustion chamber 20.

Figure 3:
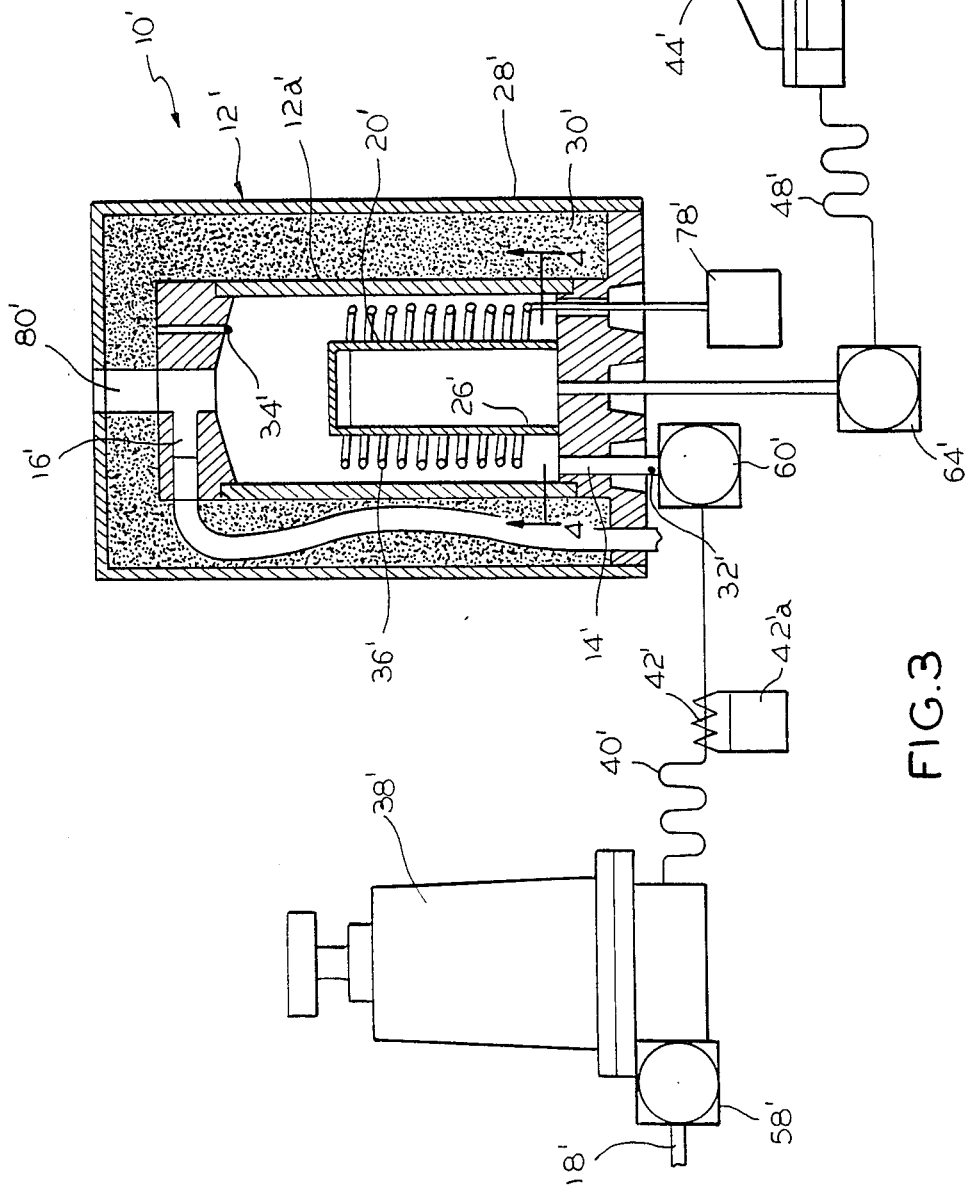
FIG. 3 is a cross-sectional view, partially schematic, illustrating an alternative embodiment of calorimeter in accordance with the present invention.

Referring to FIGS. 3 and 4, the calorimeter 10' is particularly designed for use in measuring the heating value of a medium such as steam. The calorimeter 10' which has many components in common with the calorimeter 10 previously described includes a heat exchanger 12' having a water jacket 12a' with a liquid inlet 14' and a liquid outlet 16' in spaced apart relation. As shown, the heat exchanger 12' is in communication with a source of liquid under pressure as at 18' at the liquid inlet 14' and the liquid outlet 16' is adapted to carry the liquid away from the heat exchanger 12'.

Referring specifically to FIG. 3, the calorimeter 10' includes means provided for ensuring a steady rate of flow of the liquid from the liquid inlet 14' through the heat exchanger 12' and out the liquid outlet 16' as will be described in greater detail hereinafter. The calorimeter 10' also includes a steam chamber 20' within the heat exchanger 12'. The steam chamber 20' is entirely disposed below the liquid outlet 16' so as to be submerged in the liquid when the liquid is flowing through the heat exchanger 12' at a steady rate of flow. Means are also provided for ensuring a steady rate of flow of steam to the steam chamber 20 as will be described hereinafter. In addition, the calorimeter is preferably formed such that the chamber 20' includes means such as the chamber outlets 26' for releasing steam, see also FIG. 4.

As will be appreciated, the chamber outlets 26' cause the steam to pass from the steam chamber 20' into the liquid as the liquid is flowing through the heat exchanger 12' at a steady rate of flow. The chamber outlets 26' ensure that all heat from the steam is transferred directly to the liquid. As a result, the calorimeter 10' can utilize means for measuring the difference between the first and second temperatures to accurately determine the heating value of the steam at preselected intervals or continuously.

As shown, the liquid inlet 14' is disposed at one end of the heat exchanger 12' and the liquid outlet 16' is disposed at the other end thereof with the steam chamber 20' being mounted adjacent the liquid inlet end 14'. By reason of the relative size of the steam chamber 20' and the heat exchanger 12', the steam chamber 20' will be entirely disposed below the liquid outlet 16' whereby the entire steam chamber is submerged during operation of the calorimeter 10'. In other words, the steam chamber 20' is in spaced relation to the liquid outlet end of the heat exchanger 12' which causes it to be submerged since the heat exchanger 12' is entirely filled with liquid at all times during operation.

As will be appreciated, the steam chamber 20' and the heat exchanger 12' are defined by generally cylindrical inner and outer shells preferably disposed so as to be in coaxial relation as shown in FIG. 3. The chamber outlets 26' are provided substantially entirely about the generally cylindrical shell defining the steam chamber 20' and preferably in a ring at or near the level of the liquid inlet 14'. Furthermore, the heat exchanger 12' preferably includes a water jacket 12a' disposed within a generally cylindrical reactor shell 28' which is spaced from the heat exchanger 12' to define a thermal barrier that is filled with insulation 30'.

As with the embodiment in FIG. 1, the temperature measuring means includes a first liquid temperature detecting thermistor 32' disposed at a first point in the heat exchanger 12' and a second liquid temperature detecting thermistor 34' disposed at a second point in the heat exchanger 12'. It will also be seen that means for calibrating the calorimeter 10' including a calibration heater 36' is provided for correlating known energy inputs of the heater 36' to measure the temperature increase between the first point in the heat exchanger 12' and the second point in the heat exchanger 12' whereby the calibration is then used to accurately determine the heating value of the gas. In other words, the calibration heater 36' makes it possible to calibrate the calorimeter 10' for converting a measured temperature difference between the first end or liquid inlet end 14' and the second end or liquid outlet end 16' of the heat exchanger 12' into the heating value of steam fed into the steam chamber 20'.

As will be appreciated, the steady liquid flow means includes a liquid pressure regulator 38' disposed between the source of liquid as at 18' and the liquid inlet 14' as well as a liquid capillary flow tube 40' and a liquid heater 42' intermediate the liquid pressure regulator 38' and the liquid inlet 14'. It will also be seen that the means for ensuring a steady flow of steam includes a steam pressure regulator 44' disposed between a source of steam as at 46' and the steam chamber 20' and further includes a steam capillary flow tube 48' intermediate the steam pressure regulator 44' and the steam chamber 20'. With these features, there are also preferably provided first and second liquid solenoid valves 58' and 60' and steam solenoid valves 62' and 64' provided on either side of the steady steam flow means, i.e., the steam pressure regulator 44', gas capillary flow tube 48' and gas heater 40'.

While the calorimeter 10' can be operated by manual control of the valves to measure the steam heating value, a central processing unit can advantageously achieve this objective automatically to great advantage either on demand, at selected intervals or continuously. Thus, the thermistors 32' and 34' are preferably operatively associated with a central processing unit (not shown) essentially identical to the central processing unit 74 illustrated in FIG. 1, and the central processing unit is preferably responsive to operation of the calibration heater 36' which is disposed about the steam chamber 20'. Specifically, the calibration heater 36' is linked to a control unit 78' which is located externally of the heat exchanger 12' and the central processing unit (not shown) can thus be calibrated by measuring the temperature difference of a known energy input to later convert a measured temperature difference directly to the heating value of steam in the steam chamber 20'.

Moreover, as before, the central processing unit (not shown) is preferably operatively associated with the valves 58' and 62' as well as the valves 60' and 64' to control delivery of the liquid to the heat exchanger 12' and delivery of the steam to the steam chamber 20' during operation of the calorimeter 10'. For this purpose, the central processing unit (not shown) is preferably of a conventional type which is programmable to calibrate the calorimeter 10' by setting the control unit 78' to operate the calibration heater 36' as liquid flows through the heat exchanger 12' and/or to measure the heating value of the steam as the liquid flows through the heat exchanger 12' and the steam is delivered to the steam chamber 20'.

As for the embodiment illustrated in FIGS. 3 and 4, it is well known that the heating value of steam is difficult to determine because in its vapor phase, the enthalpy can vary widely without a change in pressure or temperature. However, it is in this vaporization range where energy measurement is most often required, but steam, even at moderate pressure creates mechanical problems that have rendered this quite difficult if not impossible. However, with the embodiment illustrated in FIGS. 3 and 4, the steam can be reduced in pressure to levels compatible with good instrument design to achieve highly accurate energy measurements.

Complying with the first law of thermodynamics, the energy entering a closed system must equal the energy leaving. If expansion is performed without doing work, the enthalpy will not change which is known as reversible adibatic expansion or isentropic expansion. As previously noted, this expansion can be accomplished to very low pressure and constant low flow rates by using a two staged system, i.e., a spring loaded diaphragm pressure regulator 44' for the primary stage and an orifice or capillary tube 48' for the secondary stage.

With this arrangement, the heating medium (or steam) can be conducted directly into the measuring medium or (water). This is done exactly as the products of combustion were handled in the gas mode of the calorimeter 10. This means that the basic elements and their function will be the same with the exception of the elimination of the combustion chamber in favor of the steam chamber 20'. As a result, the burner is no longer needed in the embodiment illustrated in FIGS. 3 and 4 nor is the gas heater as supplied in the gas feed line.

With the arrangement illustrated in FIGS. 3 and 4, the heating value of the medium such as steam can be multiplied by the flow rate of the measured stream to provide the total heating value of the system.

By definition, one British Thermal Unit (BTU) is the heat required to raise one pound of water 1° Fahrenheit which makes water an advantageous liquid for use in the calorimeter 10. If gas flow is regulated to a precise constant level and all of the heat developed by burning is directed into a precisely regulated constant flow of water, then the increase in the temperature of the water will be constant and this increase may be detected and will be proportional to the BTU or Caloric value of the gas. However, the actual combustion of the gas with air as the oxidizing element is subject to some variation due to changes in the chemistry of the air.

More particularly, these variations come from the varying amount of available oxygen, the amount of inert gases and the amount of water vapor in the air. The variations have been eliminated by the present invention inasmuch as the gas is burned with pure oxygen and the amount of heat transferred into the liquid or measuring medium (which is preferably water), which would normally vary with the efficiency of the heat exchanger, has been eliminated by directing all of the products of combustion directly into the water medium. As a result, the accuracy of the process would depend upon the accuracy of the flow of the gas and water and the accuracy by which the change in the water temperature is determined.

As is well known, the accuracy of the measurement of the gas and water flow will be no better than the performance of flow meters for this purpose. However, by utilizing constant flow of water and gas, constancy rather than accuracy is the determining factor. In view of the very low flow rates required, capillary flow tubes have been utilized although flow through a sharp orifice at a constant differential pressure could be selected.

For gas measurement, there are a number of features including temperature, pressure, density, supercompressibility and viscosity which usually must be considered. By holding the pressure and temperature constant, all of the variables, except density, can be eliminated with orifice control and with a capillary flow tube, all but viscosity can be eliminated. However, with laminar control, viscosity variations will be low and will not change as much as gas density leading to the selection of capillary flow tubes for gas and oxygen.

With regard to the control of the flow of a liquid such as water, laminar control such as that achieved with a capillary flow tube is deemed preferable even though such measurement is not as difficult as for gas or oxygen.

Establishing a constant differential pressure varies with the type of pressure regulator being utilized. For both water and gas, a spring loaded diaphragm regulator is deemed desirable, although for a gas, a two-stage system is considered preferable to eliminate variables caused by pressure variations upstream. Because a liquid such as water is essentially incompressible, a single stage regulator is deemed adequate.

Temperature of the gas, oxygen and water are held constant by the use of an electric heating element in the regulated flow tube. Thus, the heaters 42, 50 and 56 which have respective controls 42a, 50a and 56a are utilized, although regulation of the temperature of the oxygen flow is not critical, but to be assured of complete combustion of the sampled gas an excess of oxygen is required and excess oxygen will not alter the final measurement. However, since the excess oxygen will accept some of the heat of combustion, this heat is returned to the liquid through the chamber outlets.

As will be appreciated, the combustion will take place in a small chamber completely submerged in the liquid medium. When started, combustion will continue at a constant back pressure defined by the head of the water chamber which is constant. The products of combustion will be discharged through small ports at the bottom of the combustion chamber. By this means, all of the products will give up all of their heat to the liquid.

More specifically, this will include the heat of condensation of the vaporized liquid component by dissolving the soluble components. The insoluble components will be small bubbles that will be at the same temperature as the water by the time they reach the gas vent port 80 at the top of the heat exchanger 12 extending through the reactor shell 28 and extending from the liquid outlet 16. While there will be some heat lost by conduction and radiation, this loss will be at a minimum by the use of thermal insulation surrounding the heat exchanger 12.

The temperature of the liquid entering and leaving the calorimeter 10 will be sensed by either thermistors or RTD's. This will provide an electrical signal proportional to the temperature difference. Calibration is accomplished by energizing an electrical heating element close to the combustion chamber. This will heat the water in the same manner as the combustion gases. Since it is fixed in resistance, the heat may be regulated by varying the current.

By this means, calibration can be achieved at any BTU level desired within the limits of the heating element. Of course, calibration can also be accomplished using a test gas of a known caloric value in place of the sampled gas.

The calorimeter as basically designed will establish a constant gas-water ratio of 0.01 cubic per minute gas to 0.1 pound water per minute. Therefore, a temperature differential of 100° between the thermistors or RTD's associated with the heat exchanger will indicate a heating value of 1,000 BTU.

The differential temperature need only to be digitized to indicate the heating value of the gas in BTU. It must be considered that the flow rates or temperatures may drift and that the loss by radiation of the instrument may change. However, these errors when they occur will automatically be removed during calibration.

As will now be appreciated, the instrument is well suited to be a continuous indicator, recorder. In order to conserve gas, oxygen and water, however, it may be programmed through the central processing unit 74 to take samples on any time basis desired or on demand. Likewise, calibration can be automatically programmed as frequently as every test or as infrequently as experience dictates.

From the foregoing, it will now be seen that in order to ensure uniform operation, constant and repeatable flow must be established in all three media, i.e., gas, oxygen and water. This control may be achieved in a variety of ways, although, in the embodiment illustrated, the primary pressure in each system is controlled by a spring loaded diaphragm regulator 38, 44 and 52. Once these pressures are established they will remain constant and repeatable since a constant and repeatable flow rate is established with the capillary tubes 40, 48 and 54.

With this arrangement, the flow will vary with the differential pressure. The upstream pressure is controlled and constant by reason of the pressure regulators 38, 44 and 52 and the downstream pressure is atmospheric plus the static head of the water medium. As a result, the differential pressure is constant and the flow rate is constant in each of the three media, i.e., gas, oxygen and water.

As will be appreciated, the gas combustion system is a combination of the mixing T fitting 70 and the mixing tube 72 in which the sampled gas and pure oxygen are thoroughly mixed. The burner 22 includes a burner tip 22a at the end of the mixing tube 72 with ignition being accomplished by a momentary electric spark in a conventional fashion. Combustion is completed within the combustion chamber 20 and the products of combustion are omitted through the plurality of chamber outlets or small ports 26 near the bottom of the combustion chamber 20.

As for the heat exchange system, the heat exchanger 12 need only include a water jacket 12a surrounding the combustion chamber 20. Water flows through this jacket 12a at a constant rate due to the water controlling system previously described. Also as previously described, the heat exchange system includes electronic temperature sensors such as the thermistors 32 and 34 at the inlet and outlet ports 14 and 16, respectively.

Referring to the calibration system, it includes the calibration heater 36 preferably in the form of an electric resistance heater. The electric resistance heater 36 is disposed within the water jacket 12a and is controlled by the central processing unit 74. As will be appreciated, the heater 36 provides means by which heat equivalent to that of combusting gas can be compared.

With regard to the central processing unit 74, it is an electronic assembly module capable of converting the differential temperature signal from the heat exchanger 12 into BTU's. It also serves to regulate the calibration heater 36. Further, the central processing unit 74 can be programmed to start and stop the entire operation of the calorimeter 10 to produce either a continuous signal or an intermittent signal of the test and calibration readings in B.T.U.'s.

As for the gas controlling system, it will be appreciated that it includes the gas pressure regulator 44, the gas capillary tube 48, the gas inlet heater 50 and the gas inlet valve 62. The gas inlet heater with its attendant controller keeps gas temperature constant to eliminate variations in flow whereas the gas inlet valve 62 is a safety device to isolate the entire gas system and to vent any leakage should it occur. The oxygen controlling system includes the oxygen pressure regulator 52, the oxygen capillary tube 54, the oxygen inlet heater 56, and the oxygen inlet valve 66. The oxygen inlet heater 56, with its attendant controller keeps oxygen temperature constant to eliminate variations in flow whereas the oxygen in the valve 66 is a safety device to isolate the entire oxygen system and to vent any leakage should it occur.

With regard to the water controlling system, it includes the water pressure regulator 38, the water capillary tube 40, the water inlet heater 42 and the water inlet valve 58. The water inlet heater with its attendant controller keeps water temperature constant to eliminate variations in flow whereas the water inlet valve 58 is a safety device to isolate the entire water system and to vent any leakage should it occur.

Referring to the gas combustion system, it comprises the gas combustion chamber 20, the gas burner 22 having gas ignition electrodes, the gas burner tip 22a, the gas mixing T-fitting 70 and the gas mixing tube 72. The heat exchange system comprises the water jacket 12a, the water inlet 14, the water outlet 16, the water inlet thermistor 32 and the water outlet thermistor 34 as well as the gas vent 80. Finally, the calibration system comprises the electric calibration heater 36 as well as the central processing unit 74.

To initiate the operation of the calorimeter 10, all six solenoid valves 58, 60, 62, 64, 66 and 68 are energized into their open position. Regulated gas, oxygen and water flow commences and an instantaneous electric spark ignites the mixture of gas and oxygen. Combustion is complete within the combustion chamber 20 with the heat of radiation and convection from the flame being received by the combustion chamber shell and conducted into the water in the water jacket 12a of the heat exchanger 12. Products of combustion including water vapor, carbon dioxide, excess oxygen and inert gas are vented through the small chamber outlets or ports 26 near the bottom of the combustion chamber 20 with the water vapor immediately condensing. Further, the water absorbs all of the soluble gases with the insoluble gases rising to the gas vent 80 with these actions permitting the acceptance of all of the heat generated by the combustion into the heat exchanger water.

During the calibration cycle, the flow of water is initiated by the water valves 58 and 60 while the gas and oxygen valves remain closed. The resistance electric heating element 36 is energized by the central processing unit 74. The energy of the electric heating element 36 may be varied and set to any BTU value desired within the limits of the instrument. The nearer the setting to the anticipated gas value the more accurate the reading obtained. The heat from the resistance electric heating element 36 is directed into the water and the temperature differential is transmitted to the central processing unit 74 resulting in a signal in BTU's exactly as produced by the combustion of the test gas.

A reference gas that is calibrated could be used to adjust the instrument but the resistance electric heating element 36 has several advantages. Among these is the fact that the calibration is directly traceable to the National Bureau of Standards by using certified instruments which are generally available in any testing laboratory including the captive laboratories of most users. Moreover, it is generally impossible to obtain a reference gas that is directly traceable in BTU value because this value is implied rather than directly measured and cost, space and convenience is saved by eliminating a reference gas.

From the above, the use of oxygen in place of air is important since oxygen speeds up the oxidizing process because it is about five times as efficient as air. Submerged combustion is also important because it eliminates thermal barriers present in other designs and ensures a minimum of heat loss. Flow control is also important because of the need for reliably constant conditions leaving little or no room for error. Finally, electric calibration is important because it represents a cross reference from one energy source to another.

While in the foregoing there have been set forth preferred embodiments of the invention, it will be appreciated that the details herein given may be varied by those skilled in the art without departing from the spirit and scope of the appended claims.

I claim:

1. A calorimeter of the liquid-flow type for measuring the heating value of a heating medium at preselected intervals or continuously, comprising:

a heat exchanger having a liquid inlet at one end thereof and a liquid outlet at the other end thereof in spaced apart relation, said heat exchanger being in communication with a source of liquid under pressure at said liquid inlet and said liquid outlet being adapted to carry said liquid from said heat exchanger, and including means for providing a steady rate of flow of said liquid through said heat exchanger;

a chamber disposed within said heat exchanger, said chamber being located adjacent said liquid inlet so as to be entirely disposed below said liquid outlet so as to be submerged in and substantially surrounded by said liquid when said liquid is flowing through said heat exchanger at said steady rate of flow, and including means for providing a steady rate of flow of said heating medium to said chamber;

said heating medium in said chamber being adapted to heat said liquid from a first temperature at said liquid inlet to a second, higher temperature at said liquid outlet as said liquid is flowing through said heat exchanger at said steady rate of flow;

said chamber including means for releasing said heating medium, said releasing means causing said heating medium to pass from a lower end of said chamber into said liquid as said liquid is flowing through said heat exchanger at said steady rate of flow, said releasing means insuring that all heat from said heating medium is transferred to said liquid; and means for measuring the difference between said first and second temperatures to determine the heating value of said heating medium.

2. The calorimeter as defined by claim 1 wherein said heating medium is gas, said chamber being a combustion chamber having a burner in communication with said gas and with a source of oxygen under pressure to be delivered to said burner for mixture with said gas and including means for providing a steady rate of flow of said oxygen to said burner, said oxygen and gas being adapted to be burned at said burner in said combustion chamber to heat said liquid from said first temperature at said liquid inlet to said second, higher temperature at said liquid outlet as said liquid is flowing through said heat exchanger at said steady rate of flow, said releasing means causing the products of combustion from burning said gas and oxygen to pass from said combustion chamber into said liquid.

3. The calorimeter as defined by claim 2 wherein said steady liquid flow means includes a liquid pressure regulator disposed between said source of liquid and said liquid inlet.

4. The calorimeter as defined by claim 3 further including a liquid capillary flow tube and a liquid heater intermediate said liquid pressure regulator and said liquid inlet.

5. The calorimeter as defined by claim 2 wherein said means providing the steady rate of flow of said heating medium includes a gas pressure regulator disposed between a source of gas under pressure and said burner.

6. The calorimeter as defined by claim 5 further including a gas capillary flow tube and a gas heater intermediate said gas pressure regulator and said burner.

7. The calorimeter as defined by claim 2 wherein said steady oxygen flow means includes an oxygen pressure regulator disposed between said source of oxygen and said burner.

8. The calorimeter as defined by claim 3 further including an oxygen capillary flow tube and an oxygen heater intermediate said means providing said steady rate of flow of said oxygen and said burner.

9. A calorimeter of the liquid-flow type for measuring the heating value of a gas on demand, at selected intervals or continuously, comprising:
a heat exchanger having a liquid inlet end and a liquid outlet end, said heat exchanger being in communication with a source of liquid under pressure at said liquid inlet end and said liquid outlet end being adapted to carry said liquid from said heat exchanger in a non-recirculating manner, and including means for providing a steady rate of flow of said liquid through said heat exchanger;
a combustion chamber having a burner and being disposed within said heat exchanger adjacent said liquid inlet end, said liquid outlet end of said heat exchanger being spaced above said combustion chamber such that said combustion chamber is entirely submerged in and substantially surrounded by said liquid and adjacent said liquid inlet end in spaced relation to said liquid outlet end when said liquid is flowing through said heat exchanger at said steady rate of flow, and including means for providing a steady rate of flow of said gas to said burner;
a source of oxygen under pressure for mixture with said gas, said oxygen and gas being adapted to be burned at said burner in said combustion chamber to heat said liquid from a first temperature at said liquid inlet end to a second, higher temperature at said liquid outlet end as said liquid is flowing through said heat exchanger at said steady rate of flow, and including means for providing a steady rate of flow of said oxygen to said burner;
said combustion chamber including means for releasing the products of combustion from burning said oxygen and gas at said burner, said releasing means being disposed adjacent said liquid inlet end of said heat exchanger and causing the products of combustion to pass from said combustion chamber into said liquid as said liquid is flowing through said heat exchanger at said steady rate of flow, said releasing means ensuring that all heat from said oxygen and gas is transferred to said liquid;
means for calibrating said calorimeter for converting a temperature difference between said liquid inlet end and liquid outlet end of said heat exchanger into the heating value of said gas; and
means for measuring the difference between said first and second temperatures;
whereby the heating value of said gas can be determined.

10. The calorimeter as defined by claim 9 wherein said temperature difference measuring means includes a first liquid temperature detecting thermistor disposed at said liquid inlet end of said heat exchanger and a second liquid temperature detecting thermistor disposed at said liquid outlet end of said heat exchanger.

11. The calorimeter as defined by claim 9 wherein said heat exchanger and combustion chamber are both defined by generally cylindrical shells, said releasing means including a plurality of chamber outlets disposed about said generally cylindrical shell of said combustion chamber.

12. The calorimeter as defined by claim 9 wherein said heat exchanger is disposed within a generally cylindrical reactor shell, said generally cylindrical reactor shell being spaced from said heat exchanger to define a thermal barrier therebetween, and including thermal insulation in said thermal barrier.

13. The calorimeter as defined by claim 9 wherein said steady liquid flow means includes a liquid pressure regulator disposed between said source of liquid and said liquid inlet, and further including a liquid capillary flow tube and a liquid heater intermediate said liquid pressure regulator and said liquid inlet.

14. The calorimeter as defined by claim 9 wherein said steady gas flow means includes a gas pressure regulator disposed between a source of gas under pressure and said burner, and further including a gas capillary flow tube and a gas heater intermediate said gas pressure regulator and said burner.

15. The calorimeter as defined by claim 9 wherein said steady oxygen flow means includes an oxygen pressure regulator disposed between said source of oxygen and said burner, and further including an oxygen capillary flow tube and an oxygen heater intermediate said oxygen pressure regulator and said burner.

16. The calorimeter as defined by claim 9 wherein said calibrating means includes a calibration heater disposed about said combustion chamber within said heat exchanger and a control unit for said calibration heater externally of said heat exchanger.

17. The calorimeter as defined by claim 9 including a mixing T-fitting having a first portion in communication with said gas, a second portion in communication with said source of oxygen and a third portion in communication with said burner.

18. The calorimeter as defined by claim 9 including a vent in communication with said heat exchanger at said liquid outlet end thereof.

19. The calorimeter as defined by claim 9 wherein said temperature difference measuring means is integrally associated with a central processing unit, said central processing unit being responsive to operation of said calibration means to relate temperature difference to heating value, said central processing unit later being responsive to burning of said gas and oxygen to convert temperature difference to the heating value of said gas.

20. The calorimeter as defined by claim 9 wherein said central processing unit is operatively associated with a valve to control delivery of said gas to said burner, a valve to control delivery of said oxygen to said burner, and a valve to control delivery of said liquid to said heat exchanger, said central processing unit being programmable to calibrate said calorimeter and/or measure the heating value of said gas on demand, at selected intervals or continuously.

21. The calorimeter as defined by claim 1 wherein said heating medium is steam and said chamber is a steam chamber from which said steam passes from said steam chamber into said liquid by reason of said releasing means.

* * * * *